United States Patent
Bergmann et al.

(10) Patent No.: US 6,355,233 B1
(45) Date of Patent: Mar. 12, 2002

(54) HAIR CARE COMPOSITIONS AND METHOD FOR DEPOSITING SWOLLEN POLYMER PARTICLES ONTO HAIR

(75) Inventors: Wolfgang Robert Bergmann, Long Grove; John Edward Wydila, Schaumburg; Paul Howard Neill, Hinsdale; Loralei Marie Brandt, Cary; Joanne Crudele, Wauconda; Chaitanya Umedbhai Patel, Glen Ellyn, all of IL (US); Christophe Michel Finel, Compiegne (FR); Walter Thomas Gibson, Cheshire; Roger Michael Lane, Heswall, both of (GB)

(73) Assignee: Unilever Home & Personal Care USA, division of Conopco, Inc., Chicago, IL (US)

( * ) Notice: Subject to any disclaimer, the term of this patent is extended or adjusted under 35 U.S.C. 154(b) by 0 days.

(21) Appl. No.: 09/310,274

(22) Filed: May 12, 1999

Related U.S. Application Data

(63) Continuation-in-part of application No. 09/092,487, filed on Jun. 5, 1998.

(51) Int. Cl.[7] .................................................. A61K 7/06
(52) U.S. Cl. ................. 424/70.12; 424/70.1; 424/70.11
(58) Field of Search ............................... 424/401, 70.1, 424/70.11, 70.21, 70.22, 70.27, 70.37, 47; 514/63

(56) References Cited

U.S. PATENT DOCUMENTS

| 4,842,850 A | * | 6/1989 | Vu |
| 4,902,499 A | * | 2/1990 | Bolish, Jr. et al. |
| 5,654,362 A | * | 8/1997 | Schulz, Jr. et al. |
| 5,721,026 A | * | 2/1998 | Feder et al. |
| 5,811,487 A | * | 9/1998 | Schulz, Jr. et al. |

FOREIGN PATENT DOCUMENTS

| EP | 0001462 | 4/1979 |
| EP | 0295903 | 12/1988 |
| EP | 0412705 | 2/1991 |
| EP | 0473039 | 3/1992 |
| EP | 0584877 | 3/1994 |
| WO | 97/38667 | * 10/1997 |

OTHER PUBLICATIONS

Zviak, The Science of Hair Care, pp56–73, 1986.*
International Search Report Application No. PCT/EP 99/03588 mailed Oct. 19, 1999.

* cited by examiner

Primary Examiner—Thurman K. Page
Assistant Examiner—Brian K. Seidleck
(74) Attorney, Agent, or Firm—Matthew Boxer

(57) ABSTRACT

A hair care composition which comprises (a) one or more polymer systems in the form of discrete particles, wherein said particles are swollen with a non-aqueous solvent; and (b) water or a hydroalcoholic solution carrier, are described. A method for treating hair which comprises contacting said hair with compositions of the invention is also described.

1 Claim, 1 Drawing Sheet

Figure 1:
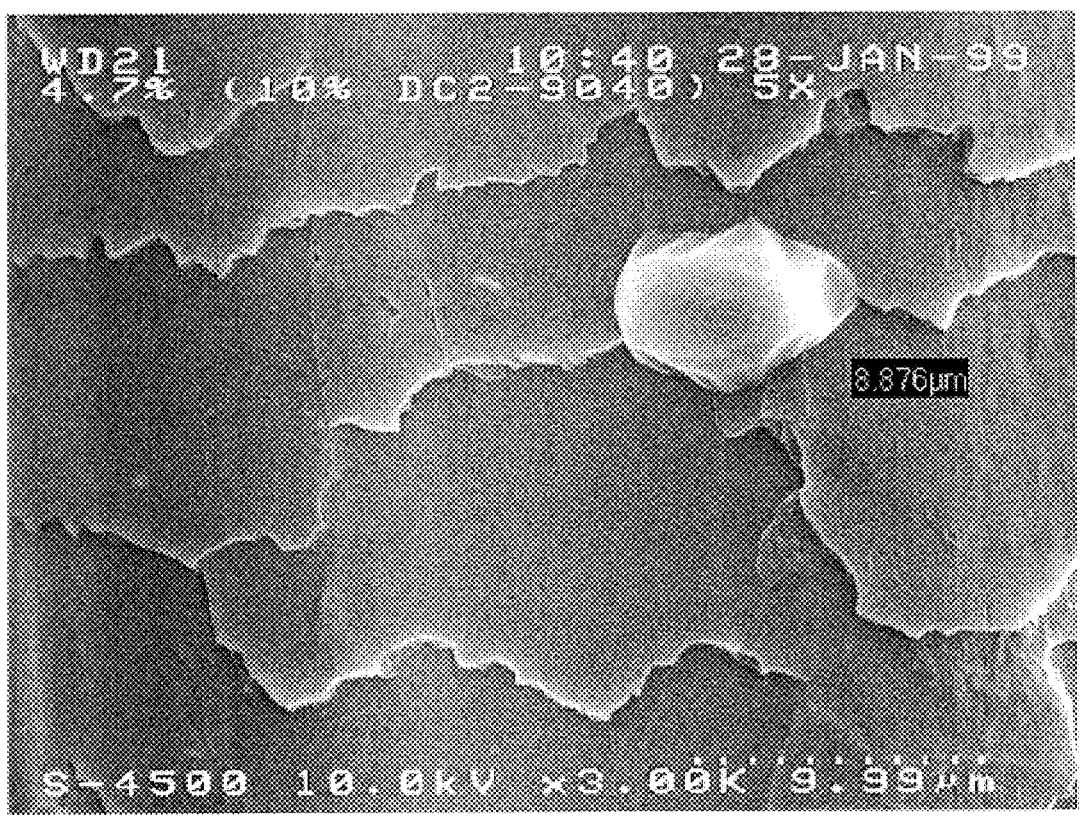

HAIR CARE COMPOSITIONS AND METHOD FOR DEPOSITING SWOLLEN POLYMER PARTICLES ONTO HAIR

RELATED CASES

This application is a Continuation-in-Part of U.S. Ser. No. 09/092,487, filed Jun. 5, 1998.

PUBLICATIONS

The following publication is cited in this application.

FOREIGN PATENT

EP 295903A; Fukuyama, Y., Kawase, J. and Yoshihara, T. "Hair preparation having high sebum absorptivity/comprises carrier and fine particulate oil absorptive compound, especially porous polyvinyl polymer, and opt. Anti-dandruff agent." Dec. 21, 1988.

FIELD OF THE INVENTION

The present invention is directed to hair care compositions and a method for conditioning and bodifying the hair. The hair care compositions which impart body to the treated hair without giving up conditioning attributes. In particular, the present invention relates to hair care compositions comprising one or more solvent-swollen polymer systems in a water or hydroalcoholic carrier, and a method for conditioning and bodifying human hair.

BACKGROUND OF THE INVENTION

In the past, it has been difficult to deliver good hair body from a hair treatment composition without giving up conditioning attributes. There is a consumer need for a conditioner to provide more than the typical conditioning attributes which include improved wet and dry combing properties; freedom from static charge buildup; enhanced feel and softness. The current conditioner technology has not successfully addressed the need for incorporating enhanced body (improved resiliency and bounce) and style creation without sacrificing the conditioning attributes.

Thus, it is an object of this invention to provide hair care compositions utilizing polymer systems which can provide improved body, resiliency and bounce while maintaining the wet and dry properties expected from conditioner.

SUMMARY OF THE INVENTION

The present invention relates to a hair conditioning composition and a method of treating hair, and more particularly to aqueous hair conditioners which contain one or more polymer systems. The hair conditioner compositions deposit swollen particles onto the hair surface rather than continuous films. The particle systems are incorporated into hair conditioning compositions in the range of 0.1 to 20%. The formulations deposit discrete swollen particles onto hair with total surface coverage ranging from 0.001 to 50%. These formulations have been demonstrated to deliver a consumer perceptible increase in hair body and style enhancement without sacrificing conditioning attributes.

More specifically, the invention relates to hair care compositions which comprise (a) one or more polymer systems in the form of discrete particles, wherein said particles are swollen with a non-aqueous solvent; and (b) water or a hydroalcoholic solution carrier.

DETAILED DESCRIPTION OF THE INVENTION

As used herein % means weight % of the total composition unless otherwise indicated. Compositions of the invention can be made by methods that are analogous to methods that are known in the art.

As used herein discrete particles means material that exists as independent, irregular or spherical masses. When referring to material deposited on a surface, discrete particles means deposited materials that are not in the form of continuous films, and have a variable thickness on the substrate surface.

As used herein swollen polymer systems means polymers that increase their volumes by absorbing compatible solvents into their structures.

As used herein total surface coverage means the percentage of total surface area of the substrate surface that is occupied by the deposited material.

FIG. 1 is a scanning electron micrograph of 3,000× magnification showing a discrete, air dried, DC-2-9040 particle on the surface of the hair fiber cuticle. The hair fibers were prepared for scanning electron microscopy as follows:

The hair fibers were treated with a composition of the present invention and which composition was rinsed from the hair. The hair fiber(s) were air dried, mounted onto an aluminum specimen holder and examined under the microscope at 10 kV. The composition of the invention that was used, was a Finesse Extra Body Conditioning base to which was added 4.7% of a mixture of 10% DC-2-9040 in cyclomethicone.

The present invention relates to aqueous hair care compositions including for example, conditioners, shampoos, hair sprays and mousses. Conditioners include rinse-off and leave-in conditioners. The invention also relates to methods of treating hair, and more particularly to treating hair with aqueous hair care compositions which contain one or more materials which deposit swollen, polymer particles on the hair. These materials can be crosslinked polymers that swell in compatible solvents, but do not dissolve in the solvent.

One aspect of this invention relates to a hair conditioning composition and a method of treating hair, and more particularly to compositions that contain one or more swollen polymer systems. These polymers are swollen with a solvent that may also be present in excess in the hair care composition of the invention. The swollen polymer systems are incorporated into hair conditioning compositions in the range of 0.1 to 20%. When the swollen polymers are dispersed within the conditioner, the swollen polymers exist as discrete swollen polymer particles in the conditioner. These hair conditioner compositions deposit swollen polymer particles onto the hair surface rather than continuous films. The formulations deposit discrete, swollen polymer particles onto hair with total surface coverage ranging from 0.001 to 50%. These formulations have been demonstrated to deliver a consumer perceptible increase in hair body and style enhancement without sacrificing conditioning attributes.

Traditional conditioners deposit their conditioning and bodifying agents as continuous films. Continuous films negatively impact body and style enhancement. The present invention, by contrast, deposits discrete particles onto the hair surface that enhance hair body, and they aid in the creation of a hairstyle.

Common wisdom held by those skilled in the art would suggest that deposition of discrete particles would lead to unacceptable sensory attributes such as excessive roughness. Surprisingly, we have found that deposition of discrete, swollen particles leads to body and style enhancement without unacceptable sensory attributes.

The one or more polymeric materials that can be included in our compositions are any polymers that deposit as discrete particles on the hair, and wherein said particles have been swollen by the uptake of solvent are also in the compositions of the present invention.

Examples of materials capable of producing swollen polymer particles include silicone polymers and surface-alkylated spherical silicon particles.

A discussion of the use of silicone polymers as the materials that deposit swollen particles when dispersed in the compositions of the invention now follows. Preferred silicone polymers for use in the invention are polydiorganosiloxanes and polymonoorganosiloxanes. The polydisorganosiloxanes are preferably derived from suitable combinations of $R_3SiO_{0.5}$ units and $R_2SiO$ units. The polymonoorganosiloxanes are preferably derived from $R_1SiO_{1.5}$. Each R independently represents an alkyl, alkenyl (e.g. vinyl), alkaryl, aralkyl, or aryl (e.g. phenyl) group. R is most preferably methyl.

The degree of crosslinking of silicone polymers affects their performance in the compositions of the invention. The preferred silicone polymers of the invention are cross-linked polydimethyl siloxanes and polymonomethyl siloxanes optionally having end groups such as hydroxyl or methyl.

One preferred polymer of the invention is DC 2-9040, a crosslinked, polydimethyl siloxane.

DC 2-9040 Cross-linking Chemistry is as follows.

The cross linker used in the DC 2-9040 is an alpha, omega aliphatic diene of the following structure: $CH_2=CH(CH_2)_xCH=CH_2$, where X ranges from 1–20. A crosslinked polymer network is formed by addition of Si—H across double bonds in the alpha, omega-diene. The following Dow Corning patent describes the DC 2-9040: U.S. Pat. No. 5,654,362. This just mentioned US patent is hereby incorporated by reference.

The degree of crosslinking of the silicone polymers is suitably from about 0.05% to about 35%, preferably being in the range of about 0.15% to about 7%, e.g. from about 0.2 to about 2%.

Suitable emulsion polymerized cross-linked silicone polymers are commercially available or can be readily made using conventional techniques well known to those skilled in the art.

The silicone polymer is swollen by mixing the polymer with a thermodynamically compatible solvent. The preferred solvents are those derived from linear low molecular weight polydimethyl siloxanes and cyclic low molecular weight polydimethyl siloxanes. The most preferred solvent is the cyclic pentamer polydimethyl siloxane.

The swollen polymer may be made into an aqueous emulsion or dispersion wherein the resulting polymer concentration is in a weight percent range of about 0.1 to about 10%.

In making our compositions, conventional means known to those skilled in the art are employed.

Another example of a swollen polymer system which can deposit as discrete swollen particles on the hair surface are the polymonomethyl siloxanes. The polymonomethyl siloxanes are marketed under the trade name Tospearl, obtainable from Toshiba Silicones, Tokyo, Japan. The preferred solvents are the linear low molecular weight polydimethylsiloxanes and the cyclic low molecular weight polydimethyl siloxanes. The most preferred solvent is the cyclic pentamer polydimethyl siloxane.

Non-aqueous solvents include amine functionalized polydimethylsiloxanes such as Dow Corning Q2-7224, Dow Corning Q2-8220; alkyl substituted polydimethylsiloxanes such as General Electric SF 1632; phenyltrimethyl polysiloxanes such as DC 566 Fluid; polydimethylsiloxanes having polypropylene side chains and/or polyethylene sidechains; and propoxylated and ethoxylated polydimethylsiloxanes such as DC 3225C; DC 5225C; DC 190; DC 193; cationic polydimethylsiloxanes such as anionic polydimethylsiloxanes; hydroxy substituted polydimethylsiloxanes such as GE SM 2725; and mixtures thereof. Also included are mixtures of the above polydimethyl siloxanes phenyl trimethylsiloxanes with aliphatic or aromatic solvent systems.

Hair care compositions include rinse-off conditioners, leave-on conditioners, shampoos and mousses, sprays, or lotions. Particularly preferred forms are conditioners having both conditioning and bodifying properties.

As set forth herein, the compositions of the invention can comprise one or more polymer systems in the form of discrete particles wherein said polymer systems are not silicone polymers or surface alkylated spherical silicone polymers. Such polymers are similarly swollen by mixing with appropriate non-aqueous solvents.

Hair conditioner compositions of the invention may comprise one or more cationic surfactants.

Examples of cationic surfactants include mono or di alkyl quaternary ammonium compounds or tri alkyl quaternary ammonium compounds. Additional surfactants include quaternary ammonium hydroxides or cetyl pyridinium hydroxides or salts thereof. Specific cationic surfactants include quaternary ammonium hydroxides, such as tetramethylammonium hydroxide, alyltrimethylammonium hydroxides wherein the alkyl group has from about 8 to 22 carbon atoms, for example octyltrimethylammonium hydroxide, dodecyltrimethylammonium hydroxide, hexadecyl trimethylammonium hydroxide, cetyltrimethylammonium hydroxide, octyldimethylbenzylammonium hydroxide, decyldimethylbenzylammonium hydroxide, stearyidimethylbenzylammonium hydroxide, didodecyidimethylammonium hydroxide, dioctadecyidimethylammonium hydroxide, tallow trimethylammonium hydroxide, cocotrimethylammonium hydroxide, cetyltrimethylammonium chloride, dicetyldimethylammonium chloride, tricetylmethylammonium chloride and the corresponding salts thereof, for example, chlorides, and mixtures thereof.

Other cationic surfactants include amidoamines, cetylpyridinium hydroxide or salts thereof, for example chlorides; or compounds selected from the group consisting of Quaternium-5, Quaternium-31, Quaternium-18, and mixtures thereof.

In hair conditioning compositions of the invention, the level of cationic surfactant is preferably 0.01 to 10%, or 0.05 to 5%, or 0.1 to 2% by weight of the composition.

Another ingredient that may be advantageously incorporated into hair treatment compositions of the invention which are conditioners is a fatty alcohol, particularly in conditioning compositions of the invention which comprise one or more cationic surfactant materials. Preferred fatty alcohols comprise from 8 to 22 carbon atoms, more particularly from 16 to 20. Examples of fatty alcohols include cetyl alcohol and stearyl alcohol. Compositions of the invention which are conditioners can include a conditioning agent such as a fatty amine, for example, stearamidopropyl dimethylamine.

Hair treatment compositions of the invention may also contain one or more conditioning agents selected from the group consisting of cationic polymers, protein hydrolyzates and quaternized protein hydrolyzates, and mixtures thereof.

Another preferred hair treatment composition in accordance with the invention is a shampoo composition which, in addition to the silicone polymer further comprises a surfactant to provide a deterging benefit. The deterging surfactant is selected from anionic, nonionic, amphoteric and zwitterionic surfactants, and mixtures thereof.

Suitable anionic surfactants include the alkyl sulphates, alkyl ether sulfates, alkyl aryl sulfonates, alkyl isethinates, alkyl succinates, alkyl sulphosuccinates, n-alkyl sarcosinates, alkyl phosphates, alkyl ether sulphonates, alkyl ether carboxylates and alpha-olefin sulphonates, especially their sodium, magnesium, ammonium, and mono-, di-, and tri-ethanolamine salts. The alkyl and acyl groups generally contain from 8 to 18 carbon atoms and may be unsaturated. The alkyl ether sulphates, alkyl ether phosphates and alkyl ether carboxylates may contain from one to ten ethylene oxide or propylene oxide units per molecule, and preferably contain 2 to 3 ethylene oxide units per molecule. The above anionic surfactants may be used alone or in combination with each other.

Examples of suitable anionic surfactants include sodium oleyl succinate, ammonium lauryl sulphosuccinate, ammonium lauryl sulphate, sodium dodecylbenzene sulphonate, triethanolamine dodecylbenzene sulphonate, sodium cocoyl isothionate, sodium lauryl sulphate, sodium lauryl isothionate and sodium lauryl sarcosinate. The most preferred anionic surfactants are sodium lauryl sulphate, triethanolamine lauryl sulphate, triethanolamine monolauryl phosphate, sodium lauryl ether sulphate 1 EO, 2EO, and 3EO, ammonium lauryl sulphate and ammonium lauryl ether sulphate 1 EO, 2EO, 3EO, and mixtures thereof.

Nonionic surfactants suitable for use in compositions of the invention may include condensation products of aliphatic (8 to 18 carbons) primary, secondary linear or branched chain alcohols or phenols with alkylene oxides, usually ethylene oxide and generally having from 6 to 30 ethylene oxide groups. Other suitable nonionics include alkanolamides. Examples include coco mono-diethanolamide and coco mono-isopropanolamide, and mixtures thereof.

Amphoteric and zwitterionic surfactants suitable for use in compositions of the invention may include alkyl amine oxides, alkyl betaines, alkyl amidopropyl betaines, alkylsulphobetaines, alkyl glycinates, alkyl carboxyglycinates, alkyl amphopropionates, alkylamphoglycinates, alkyl amidopropyl hydroxysultaines, acyl taurates and acyl glutamates, wherein the alkyl and acyl groups have from 8 to 19 carbon atoms. Examples include lauryl amine oxide, cocodimethyl sulphopropyl betaine, lauryl betaine, cocamidopropyl betaine and sodium cocamphopropionate, and mixtures thereof.

The surfactants are present in shampoo compositions of the invention in an amount from 0.1% to 50% by weight, preferably 0.5% to 30% by weight.

A further optional component of compositions of the invention which are shampoos, is a deposition aid, generally present at 0.001% to 5%. Examples of such deposition aids include polyquaternium-16; cationic guars, and polymer JR resins.

Compositions of the invention which are shampoos may further comprise from 0.1 to 5% of a suspending agent such as Carbopol 910, Carbopol 940, Carbopol 941, acrylate copolymers, or saccharides.

Small quantities of surfactant ranging anywhere from 0.1 to about 10%, preferably from 0.1 to about 1%, may be present in the hair mousse compositions of the invention. The surfactant may be anionic, nonionic or cationic emulsifier. Surfactants which are suitable for mousses include, for example, sodium cocoyl isethionate and Laureth-20.

Depending on the type of composition employed, one or more additional ingredients conventionally incorporated into hair treatment compositions may be included in compositions of the invention. Such additional ingredients include styling agents such as resins and hair-setting polymers, perfumes, dyes, buffering or pH adjusting agents, viscosity modifiers, opacifiers, pearlescers, preservatives, antibacterial agents, antidandruff agents, foam boosters, proteins, moisturizing agents, herb or other plant extracts and other natural ingredients.

Compositions of the invention can include a pH buffer like citric acid.

Compositions of the invention can include a dispersing agent such as water-insoluble alkyl esters and derivatives such as PPG2 Myristyl ether propionate, or cyclomethicone, dimethicone or polyhydric compounds such as glycerin.

Compositions of the invention can optionally include an opacifier.

Compositions of the invention may comprise: a swollen polymer particle system at a range of about 0.1 to about 20%; a non-aqueous solvent not included in the swollen polymer particle system at a range of about 0.1 to about 10%; water at a range of about 85 to about 94%; a cationic quaternary ammonium compound at a range of about 0.5 to 5%; and a long chain fatty alcohol at a range of about 0.5 to 10%.

Our invention includes a method for giving hair unexpected body as well as conditioning which comprises treating said hair with compositions of the invention.

The following examples serve to illustrate and not to limit the scope of the present invention.

EXAMPLE FORMULATIONS

All the examples were prepared using softened or deionized water. As used herein, benchmark means control.

Swollen particles can be utilized alone or in combination as the below examples show.

| Compositions | Benchmark % Actives | Ex. K % Active | Ex. L % Active | Ex M % Active |
|---|---|---|---|---|
| Stearamidopropyl Dimethylamine | 0.50 | 0.50 | 0.50 | 0.50 |
| Liquid Citric Acid | 0.092 | 0.092 | 0.092 | 0.092 |
| Propylene Glycol | 0.50 | 0.50 | 0.50 | 0.50 |
| Dicetyldimonium Chloride | 1.43 | 1.43 | 1.43 | 1.43 |
| Stearyl Alcohol and Ceteareth-20 | 1.00 | 1.00 | 1.00 | 1.00 |
| Cetyl Alcohol | 3.25 | 3.25 | 3.25 | 3.25 |
| Silicone Fluid 245 | 1.80 | 7.88 | 1.80 | 1.80 |
| Dimethicone | 0.10 | 0.10 | 0.10 | 0.10 |
| DC 2-9040 (16% actives) | | 4.7 | | 4.7 |
| Polymonomethyl siloxane (4.5 um) | | | 0.75 | 0.75 |
| Water | qs to 100 | qs to 100 | qs to 100 | qs to 100 |

Test 1 Preparation and Sensory Evaluation of Samples on Tresses for Rinse off Products 1. Wash 2 g tresses with 1 ml Suave® Strawberry Shampoo for thirty seconds, rinse with 45° C. water at constant flow for thirty seconds.

2. Apply 0.5 ml conditioner to the tress and massage into the hair.
3. After one minute, rinse the tress for thirty seconds as in step 1.
4. Evaluate wet combing with a small toothcomb versus control.
5. Dry tresses with a blow dryer.
6. Dry combing is evaluated with a small toothcomb and ranked from easiest combing to more difficult.
7. The overall dry character of the tress is evaluated by using the fingers.
8. Tresses were next curled with a hot curling iron for 20 seconds. The bounce or curl memory was then ranked.
9. Attributes are force ranked from 1=best to 5=worst.

TABLE 1

Sensory properties of swollen particle conditioners versus a control conditioner and bleached untreated hair.

| Example | Wet Combing | Dry Combing | Dry Feel | Curl Memory |
|---|---|---|---|---|
| Untreated | 5 | 5 | 5 | 5 |
| Control | 2 | 3 | 4 | 4 |
| K | 1 | 1 | 1 | 3 |
| L | 4 | 4 | 3 | 2 |
| M | 3 | 2 | 2 | 1 |

From Table 1, the curl memory is enhanced through the addition of swollen particles on the hair without affecting conditioning attributes.

Examples of Leave-in Conditioners

| Compositions | Ex. N % Active | Ex O % Active | Ex P % Active |
|---|---|---|---|
| Stearamidopropyl Dimethylamine | 0.50 | 0.50 | 0.50 |
| Liquid Citric Acid | 0.092 | 0.092 | 0.092 |
| Propylene Glycol | 0.50 | 0.50 | 0.50 |
| Dicetyldimonium Chloride | 1.43 | 1.43 | 1.43 |
| Stearyl Alcohol and Ceteareth-20 | 1.00 | 1.00 | 1.00 |
| Cetyl Alcohol | 3.25 | 3.25 | 3.25 |
| Dimethicone | 0.10 | 0.10 | 0.10 |
| DC 2-9040 (16% actives) | | | 4.7 |
| Polymonomethyl siloxane (2.0 um)/Cyclomethicone blend (15%) | 3.34 | 3.34 | 3.34 |
| Water | qs to 100 | qs to 100 | qs to 100 |

Test 2 was the same method as described in Test 1 with conditioner allowed to remain on the hair.

TABLE 2

Sensory properties of swollen particle conditioners on hair versus a control conditioner and bleached untreated hair.

| Example | Wet Combing | Dry Combing | Dry Feel | Curl Memory |
|---|---|---|---|---|
| Untreated | 5 | 5 | 5 | 5 |
| Control | 2 | 3 | 4 | 4 |
| N | 1 | 1 | 1 | 2 |
| O | 4 | 4 | 3 | 1 |
| P | 3 | 2 | 2 | 3 |

Table 2 shows that the addition of swollen particles can enhance the wet and dry properties and enhance curl memory as a leave-in conditioner as well.

Salon and Consumer Testing of Conditioning and Body Attributes

The following examples were prepared for consumer studies.

Examples Q and R

| Compositions | Benchmark % Active | Ex. Q % Active | Ex. R % Active |
|---|---|---|---|
| Stearamidopropyl Dimethylamine | 0.50 | 0.50 | 0.50 |
| Liquid Citric Acid | 0.092 | 0.092 | 0.092 |
| Propylene Glycol | 0.50 | 0.50 | 0.50 |
| Dicetyldimonium Chloride | 1.43 | 1.43 | 1.43 |
| Stearyl Alcohol and Ceteareth-20 | 1.00 | 1.00 | 1.00 |
| Cetyl Alcohol | 3.25 | 3.25 | 3.25 |
| Silicone Fluid 245 | 1.80 | 7.88 | 1.80 |
| Dimethicone | 0.10 | 0.10 | 0.10 |
| DC 2-9040 (16% actives) | | 1.50 | |
| Silicone Gum Blend 33/67 | | | 1.5 |
| Water | qs to 100 | qs to 100 | qs to 100 |

Salon Blitz Testing

The following Salon Blitz Testing table is a summary of the results from a series of salon tests conducted over a period of approximately 12 weeks. The benchmark for these studies is the best selling commercial extra body conditioner in the North American market. These data indicated that the formulations containing DC 2-9040 (ExQ.) outperformed the Benchmark formulation in both overall conditioning and in its ability to deliver hair body as reported by the models. The Silicone Gum Blend 33/67 (Ex. R) did not show any body attribute benefit over the benchmark.

Test 3—Salon Blitz

Salon Blitz utilized female conditioner users as the panelists. A professional hair stylist applied the test product to half of the head and the benchmark product to the other side of the panelist's head. Once product has been applied, the stylist distributed the product evenly and rinsed it out taking care to keeping both sides separated. The panelists then dry and style their own hair. A questionnaire was provided to each panelist asking them to rate (on a 9 point scale) hair characteristics (e.g. conditioning and body) for both the left and right side of the head. Higher values for key characteristics such as conditioning or body indicates a higher intensity for these attributes and therefore better performance on the hair. At least 17 panelists (n=17 to 92) were recruited for each test product evaluation. Results for this test are shown in Table 3.

TABLE 3

Salon testing of examples Q and R versus benchmark conditioner.

| Attribute | Benchmark (n = 92) | Ex. Q (n = 45) | Ex. R (n = 17) |
|---|---|---|---|
| Conditioning Attribute | 6.6 | 6.7 | 6.3 |
| Body Attribute | 5.9 | 6.2 | 6.0 |

The above table shows that Example Q delivered body without affecting conditioning performance.

Consumer Sensory Testing

The data presented in table 4 below summarizes the conditioning and body attribute results from a larger scale take home study. Again the formulation containing DC-9040 was demonstrated to provide superior conditioning and body benefit versus the commercial body conditioner. These data confirm the results from the smaller salon test described above.

The below test results were obtained by using the following method:

Test 4 Consumer Sensory Test (CST)

The CST format utilized female conditioner users n a home use study. The benchmark or prototype samples were randomly distributed to the panelists. The samples were blinded to avoid any branding bias. Each participant took the sample home and used it for a one-week period. After the one-week usage period, the panelist filled out a questionnaire regarding performance characteristics. This questionnaire was based upon a nine point rating scale (1=low to 9=high). A second sample was then provided to the participant and used for one week. At the completion of the second week, the panelist filled out an identical questionnaire asking them to rate (same scale) the characteristics of the second sample. At least 50 panelists (n ranged from 52–57) were recruited for each test product evaluation. Higher values for key characteristics such as conditioning or body indicated a higher intensity for these attributes.

TABLE 4

Consumer Sensory Test

|  | Benchmark (n = 57) | Example Q (n = 52) |
|---|---|---|
| Conditioning Attribute | 5.3 | 6.0 |
| Body Attributes | 5.1 | 5.5 |

From table 4, it was shown that body attributes were enhanced with Example Q without sacrificing conditioning benefits.

Rinse Off Compositions

| Compositions | Benchmark % Active | Ex. A % Active | Ex. B % Active | Ex. C % Active |
|---|---|---|---|---|
| Stearamidopropyl Dimethylamine | 0.50 | 0.50 | 0.50 | 0.50 |
| Liquid Citric Acid | 0.092 | 0.092 | 0.092 | 0.092 |
| Propylene Glycol | 0.50 | 0.50 | 0.50 | 0.50 |
| Dicetyldimonium Chloride | 1.43 | 1.43 | 1.43 | 1.43 |
| Stearyl Alcohol and Ceteareth-20 | 1.00 | 1.00 | 1.00 | 1.00 |
| Cetyl Alcohol | 3.25 | 3.25 | 3.25 | 3.25 |
| Cyclomethicone 245 | 1.80 | 7.88 |  | 1.80 |
| Dimethicone | 0.10 | 0.10 | 1.80 | 0.10 |
| DC 2-9040 (16% actives) |  | 9.38 |  |  |
| Poly mono methyl siloxane (2.0 um) |  |  | 0.75 |  |
| Poly mono methyl siloxane (4.5 um) |  |  |  | 0.75 |
| Water | Qs to 100 | qs to 100 | qs to 100 | qs to 100 |

*Tospearl is a polymonomethyl siloxane supplied by Toshiba Silicone Co., Tokyo, Japan.

Manufacturing Instructions

1. Add water and heat to 70–75° C.
2. Add Stearyl Alcohol and Ceteareth-20, Cetyl Alcohol, Stearamidopropyl Dimethylamine, and Citric Acid and mix until homogeneous and free of particles.
3. Cool batch to 25° C.
4. Add swollen premix of silicone fluid and either DC 2-9040 or polymonomethyl siloxane, or mixtures thereof.

The following examples are leave-in conditioners. These samples were made similarly to the examples above.

Leave-in Conditioners

| Compositions | Ex. D % Active | Ex. E % Active | Ex. F % Active |
|---|---|---|---|
| Stearamidopropyl Dimethylamine | 0.50 | 0.50 | 0.50 |
| Liquid Citric Acid | 0.092 | 0.092 | 0.092 |
| Stearyl Alcohol and Ceteareth-20 | 1.00 | 1.00 | 1.00 |
| Cetyl Alcohol | 1.50 | 1.50 | 1.50 |
| Cyclomethicone 245 | 1.80 | 1.00 | 1.00 |
| DC 2-9040 (16% actives) | 1.50 |  | 1.50 |
| Poly mono methyl siloxane (2.0 um) |  | 0.38 |  |
| Poly mono methyl siloxane (4.5 um) |  |  | 0.38 |
| Water | qs to 100 | qs to 100 | Qs to 100 |

Example formulations of Shampoo/2-in-1

| Compositions | Ex. G % Active | Ex. H % Active | Ex. I % Active |
|---|---|---|---|
| Sodium Laureth Sulfate (2 mol EO) | 12.5 |  |  |
| Cocamide DEA | 4.00 |  |  |
| Carbopol 980* |  | 0.40 | 0.40 |
| Citric Acid, 50% | 0.15 |  |  |
| Sodium Hydroxide, 50% |  | 0.25 | 0.25 |
| Blend of SLES and Cocamidopropyl betaine, 60% |  | 28.00 | 28.00 |
| Sodium Chloride |  | 0.10 | 0.10 |
| Propylene Glycol |  | 0.50 | 0.50 |
| Guar and hydroxypropyl trimonium chloride |  | 0.10 | 0.10 |
| Mica and titanium dioxide |  | 0.15 | 0.15 |
| Dimethiconol and TEA-dodecylbenzenesulfonate |  | 0.50 | 0.50 |
| DC 2-9040 (16% actives) | 1.50 | 3.00 |  |
| Polymonomethyl siloxane (4.5 um) |  |  | 0.38 |
| Water | qs to 100 | qs to 100 | qs to 100 |

Manufacturing Instructions for Example G:

1. Into a separate vessel add water.
2. With moderate mixing add Sodium Laureth Sulfate (2 mole E.O.), Cocamide DEA, and Citric acid.
3. Add sheared DC 2-9040 or add polymonomethyl siloxane.
4. Continue to cool batch.

Manufacturing Instructions for Example H and I:

1. Into a separate vessel, add water.
2. Disperse Carbopol and neutralize with sodium hydroxide.
3. Add blend of SLES and Cocamidopropyl betaine.
4. Add sodium chloride.
5. Add premix of guar hydroxypropyl trimonium chloride and propylene glycol.

6. Add remaining ingredients.

Example J Mousse

| Composition | Concentration, % Active |
|---|---|
| Stearamidopropyl Dimethylamine | 0.50 |
| Stearyl Alcohol and Ceteareth-20 | 1.00 |
| DC 2-9040 | 1.50 |
| PPG-2 Myristyl Ether Propionate | 1.00 |
| Cetyl Alcohol | 3.25 |
| Silicone Fluid 245 | 1.80 |
| Propellant HC 50 | 10.0 |
| Citric Acid | 0.092 |
| Water | qs to 100% |

Manufacturing Instructions

1. Add water and heat to 70–75° C.
2. Add Stearyl Alcohol and Ceteareth-20, Cetyl Alcohol, Stearamidopropyl Dimethylamine, and Citric Acid and mix until homogeneous and free of particles.
3. Cool batch to Cool to 50° C. and add sheared D 2-9040, Silicone Fluid 245 and Citric Acid 25° C.
4. Add swollen premix of silicone fluid and either DC 2-9040 or poly mono methyl siloxane or mixtures thereof.
5. Charge propellant.

We claim:

1. A hair care composition which comprises (a) one or more polymer systems in the form of discrete polymers of cross-linked polydimethyl siloxane, wherein said polymers have absorbed one or more compatible non-aqueous solvents into their structure so as to increase their volumes, and (b) water or hydroalcoholic solution carrier; and wherein said cross-linked polydimethyl siloxanes have as a cross-linker an alpha, omega, aliphatic diene of the following structure:

$$CH_2=CH(CH_2)_xCH=CH_2,$$

wherein x ranges from 1–20; and wherein said non-aqueous solvent is a linear or cyclic polydimethyl siloxane having a viscosity of about 0.5 to about 50 centistokes or mixtures thereof.

* * * * *